(12) United States Patent
Alvarado

(10) Patent No.: US 7,667,033 B2
(45) Date of Patent: *Feb. 23, 2010

(54) COMPOSITIONS AND METHODS FOR THE USE OF FMOC DERIVATIVES IN DNA/RNA SYNTHESIS

(75) Inventor: Gabriel Alvarado, San Mateo, CA (US)

(73) Assignee: Syngen, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/051,784

(22) Filed: Mar. 19, 2008

(65) Prior Publication Data

US 2009/0171076 A1    Jul. 2, 2009

Related U.S. Application Data

(63) Continuation of application No. 11/716,181, filed on Mar. 9, 2007, now abandoned, which is a continuation of application No. 10/670,015, filed on Sep. 24, 2003, now Pat. No. 7,534,872.

(60) Provisional application No. 60/414,061, filed on Sep. 27, 2002.

(51) Int. Cl.
   *C07H 21/00* (2006.01)
   *C07H 21/04* (2006.01)
   *C12Q 1/68* (2006.01)

(52) U.S. Cl. ............ 536/25.3; 536/23.1; 536/24.3; 435/6

(58) Field of Classification Search ............ 435/6; 536/23.1, 24.3, 25.3

See application file for complete search history.

(56) References Cited

U.S. PATENT DOCUMENTS

| 4,683,195 A | 7/1987 | Mullis et al. |
| 4,683,202 A | 7/1987 | Mullis et al. |
| 4,849,513 A | 7/1989 | Smith et al. |
| 5,015,733 A | 5/1991 | Smith et al. |
| 5,118,800 A | 6/1992 | Smith et al. |
| 6,469,158 B1 | 10/2002 | Usman et al. |
| 6,534,639 B1 | 3/2003 | Manoharan et al. |

OTHER PUBLICATIONS

Bergermann & Pfleiderer, *Helvetica Chimica ACTA*, 77:203-215 (1994).
Doty et al., *Proc. Natl. Acad. Sci. USA*, 46:461-476 (1960).
Gaur et al., *Indian Journal of Chemistry*, 29B:108-112 (1990).
Marmur & Lane, *Proc. Natl. Acad. Sci. USA*, 46:453-461 (1960).
Koole et al., *J. Org. Chem.*, 54:1657-1664 (1989).
Seela & Wenzel, *Helvetica Chimica ACTA*, 78:833-846 (1995).
Alvarado et al., "Direct Immobilization of Oligonucleotides on Polymer Supports. Use of FOMC Derivative in DNA/RNA Synthesis. Methods for Using Immobilized Oligonucleotides." *Innovations and Persepctive in Solid Phase Synthesis and Combinatorial Libraries*, Editor Roger Uptin, Chapter 9, pp. 37-42 (2000).
Wallace et al., *Biochimie*, 67:755-762 (1985).

*Primary Examiner*—Jezia Riley
(74) *Attorney, Agent, or Firm*—King & Spalding LLP

(57) ABSTRACT

Methods of nucleic acid preparation are described, including preparation of MnRNA, using FMOC derivatives to synthesize oligonucleotides in addition to applying FMOC protocols to various therapeutic and diagnostic methods. In some embodiments a single stranded oligonucleotide is synthesized bound to a polymer support (such as optic fiber glass filters) using said FMOC derivatives.

4 Claims, 5 Drawing Sheets

1) 0.05M DBU/py or CH₃CN
a) 1:1 molar ratio of DBU to compound 1
b) 1:10 molar ratio of DBU to compound 1

1

Retention time in min.

Starting material

A Fmoc    (16.3min)
A Fmoc2   (17.8min)
C Fmoc    (17.0min)
G Fmoc    (15.5min)
G Fmoc2   insoluble in DBU/CH₃CN
          de-protection repeated with 0.05 M DBU/Py Product                    Dibenzofulvene B=A (13.0min)              (16.8min)
   A (13.0min)             (16.8min)
   C (13.1min)             (17.0min)
   G (12.4min)             (16.9min)

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
cggccggccg gccggccggc cggc                                          24

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
gcggcgcggc gcggc                                                    15

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3

```
tctgcggcgt ctgcggcg                                          18
```

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4

```
gcgccccgcg cgccccgc                                          18
```

COMPOSITIONS AND METHODS FOR THE USE OF FMOC DERIVATIVES IN DNA/RNA SYNTHESIS

This patent application is a continuation of U.S. patent application Ser. No. 11/716,181 filed on Mar. 9, 2007 now abandoned, which is a continuation of U.S. patent application Ser. No. 10/670,015 filed on Sep. 24, 2003 now U.S. Pat. No. 7,534,872, which claims priority to U.S. Provisional Patent Application No. 60/414,061 filed Sep. 27, 2002, both of which are incorporated herein in their entirety by reference.

TECHNICAL FIELD

The present invention relates to compositions and methods using FMOC derivatives in DNA/RNA synthesis and in particular the use, in a variety of formats, of immobilized oligonucleotides.

BACKGROUND

More than twenty years ago the first gene was synthesized by means of traditional chemical methods. These traditional methods relied on the use of protecting reagents for those reaction groups in nucleosides and nucleotides which are sensitive to the condensing agents required to form the phosphodiester bounds. These sensitive groups include the amino groups of the bases, the 3'- and 5'-hydroxy groups of the deoxyribose, and the phosphate group itself. Additionally, these traditional methods of nucleic acid synthesis relied on supports and linker compounds as an anchor for the nascent nucleic acid strand.

In many applications, it is desirable to have the nucleic acid strand released from the linker support. This cleavage is usually accomplished at the linker through chemical treatment that leads to the removal of certain groups and the resultant release of the nucleic acid from the support. Thus various methods have been developed to bind the beginning of the nucleic acid strand to the solid support via a linker that is susceptible to cleavage by chemical treatment, as well as methods for the efficient release of undamaged nucleic acid strand from the anchor.

These traditional approaches, however, are cumbersome and time consuming in terms of resulting percentage yield of the desired product (e.g. DNA and/or RNA). What is needed, therefore, is a more efficient and versatile method for nucleic acid synthesis.

SUMMARY

A key step in the solid support synthesis of oligonucleotides is the protection of exocyclic amino groups of 2'-deoxyadenosine, 2'-deoxycytidine and 2'-deoxyguanosine. The known N-acyl residues, synthesis by the phosphorotriester, H-phosphonate and phosphoramidite methods. These groups are relatively stable under neutral and acidic conditions. However, their rates of removal under alkaline conditions are dependant upon the nature of base residues and therefore the full deprotection period of the resulting oligonucleotide is too long.

To cure this problem the Applicants used, in some embodiments, labile 9-fluorenylmethoxycarbonyl group (FMOC) for the protection of the exocyclic amino functions of deoxynucleoside bases. In addition, the Applicants incorporated the use of FMOC under synthesis conditions of the monomeric building blocks and their corresponding phosphoramidites. That is to say, as illustrated in FIG. 1, the fully protected FMOC deoxynucleoside phosphoramidites and their corresponding FMOC derivatized polymer supports were used in the synthesis of different DNA/RNA chains.

In selected embodiments, the Applicants use this DNA/RNA synthetic motif in novel adaptations of various diagnostic and therapeutic methods. These methods include, but are not limited to, the improved synthesis of antisense compounds, high throughput DNA synthesis, the preparation of labeled nucleic acids, and the preparation and use of multifuntional columns comprising oligonucleotides bound to a polymer support.

In one embodiment, the present invention describes a method for synthesizing and purifying an oligonucleotide immobilized on a solid support complex, comprising: a) providing: i) a polymer support, and ii) four pools of deoxyribonucleoside 3'-phosphoramidite monomers in solution, wherein at least one of said monomers contains 9-fluorenylmethoxycarbonyl as an amino protecting group; b) sequentially contacting said polymer support with a solution of monomers from one or more of said four pools under conditions such that a sequence of monomers is immobilized on said polymer support to generate an oligonucleotide/polymer support complex, wherein said complex comprises at least one monomer containing 9-fluorenylmethoxycarbonyl and wherein said solution, after said contacting, comprises unreacted material; c) treating said complex under conditions such that said unreacted material is substantially removed, thereby creating a purified oligonucleotide/polymer support complex, and d) treating said purified oligonucleotide/polymer support complex under conditions whereby said 9-fluorenylmethoxycarbonyl is released.

In one embodiment, the above referenced method using said deoxyribonucleoside 3'-phosphoramidite monomer containing 9-fluorenylmethoxycarbonyl as an amino protecting group is a 9-fluorenylmethoxycarbonyl-2'-deoxycytidine 3'-phosphoramidite. In one embodiment, the above referenced method using said deoxyribonucleoside 3'-phosphoramidite monomer containing 9-fluorenylmethoxycarbonyl as an amino protecting group is a 9-fluorenylmethoxycarbonyl-2'-deoxyadenosine 3'-phosphoramidite.

In one embodiment, the above referenced method using said deoxyribonucleoside 3'-phosphoramidite monomer containing 9-fluorenylmethoxycarbonyl as an amino protecting group is a 9-fluorenylmethoxycarbonyl-2'-deoxyguanosine 3'-phosphoramidite.

Definitions

To facilitate understanding of the invention, a number of terms are defined below.

A "solvent" is a liquid substance capable of dissolving or dispersing one or more other substances. It is not intended that the present invention be limited by the nature of the solvent used.

As used herein, when a solution passes through a polymer support, it comprises the "flow through." Material that does not bind, if present, passes with the solution through the polymer support into the flow through. To eliminate all nonspecific binding, the polymer support is "washed" with one or more wash solutions which, after passing through the polymer support, comprise one or more "effluents." "Eluent" is a chemical solution capable of dissociating material bound to the matrix (if any); this dissociated material passes through the matrix and comprises an "eluate."

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes is formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., Biochimie 67:755 (1985). In the case of radioactive oligonucleotide probes, only extremely high specific activities are found to show satisfactory results. See Studencki and Wallace, DNA 3:1 (1984) and Studencki et al., Human Genetics 37:42 (1985).

K. B. Mullis et al., U.S. Pat. Nos. 4,683,195 and 4,683,202, hereby incorporated by reference, describe a method for increasing the concentration of a segment of a target sequence in a mixture of genomic DNA without cloning or purification. This process for amplifying the target sequence (which can be used in conjunction with the present invention to make target molecules) consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g. hybridization with a labeled probe; incorporation of biotinylated primers followed by avidin-enzyme conjugate detection; incorporation of $^{32}P$ labeled deoxynucleotide triphosphates, e.g., dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The PCR amplification process is known to reach a plateau concentration of specific target sequences of approximately $10^{-8}$ M. A typical reaction volume is 100 µl, which corresponds to a yield of $6 \times 10^{11}$ double stranded product molecules.

With regard to complementarity, it is important for some diagnostic applications to determine whether the hybridization represents complete or partial complementarity. For example, where it is desired to detect simply the presence or absence of pathogen DNA or RNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), methods that allow for the same level of hybridization in the case of both partial as well as complete complementarity are typically unsuited for such applications; the probe will hybridize to both the normal and variant target sequence. Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art. As indicated by standard references, an estimate of the $T_m$ value may be calculated by the equation:

$$T_m = 81.5° \text{ C.} + 16.6 \log M + 0.41(\% \; GC) - 0.61(\% \text{ form}) - 500/L$$

where M is the molarity of monovalent cations, % GC is the percentage of guanosine and cytosine nucleotides in the DNA, % form is the percentage of formamide in the hybridization solution, and L=length of the hybrid in base pairs. [See, e.g., Guide to Molecular Cloning Techniques, Ed. S. L. Berger and A. R. Kimmel, in Methods in Enzymology Vol. 152, 401 (1987)]. Other references include more sophisticated computations which take structural as well as sequence characteristics into account for the calculation of $T_m$.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Such labels can be added to the oligonucleotides of the present invention.

The terms "nucleic acid substrate" and nucleic acid template" are used herein interchangeably and refer to a nucleic acid molecule which may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

The term "polymer support", as used herein, refers to any substrate or solid support having the chemical composition (or demonstrating the physical properties of) a polymer. Examples of a polymer support include (but are not limited to) silica, glass, polystyrene, or optic fiber glass filters.

As used herein, the abbreviation "DBU" refers to 1,8-diazabicyclo[5.4.0] undec-7-ene.

As used herein, the abbreviation "FMOC" refers to a chemical compound comprising a 9-fluorenylmethoxycarbonyl [also known as (fluoren-9-yl)methoxycarbonyl] group.

As used herein, the term "unreacted material" refers to reagent(s) that are not consumed in a chemical reaction. Examples of unreacted materials include (but are not limited to) unincorporated monomers of deoxyribonucleosides after the synthesis of an oligonucleotide.

As used herein, the term "purified oligonucleotide/polymer support complex" refers to a oligonucleotide/polymer support complex wherein said oligonucleotide is at least 70% pure, more preferably at least 80% pure, and still more preferably at least 90% pure.

As used herein the term "substantially removed" refers to a reaction mixture, after a chemical reaction, wherein unreacted materials and/or unwanted reaction by products are removed, thereby, leaving a desired product(s) that is at least 70% pure, more preferably at least 80% pure, and still more preferably at least 90% pure As used herein, the words "pool" or "pools" refer to a contained source of reagent. Example of a pool(s) include (but are not limited to) a solution of 2'-deoxycytidine 3'-phosphoramidite.

DETAILED DESCRIPTION

Figure 1:
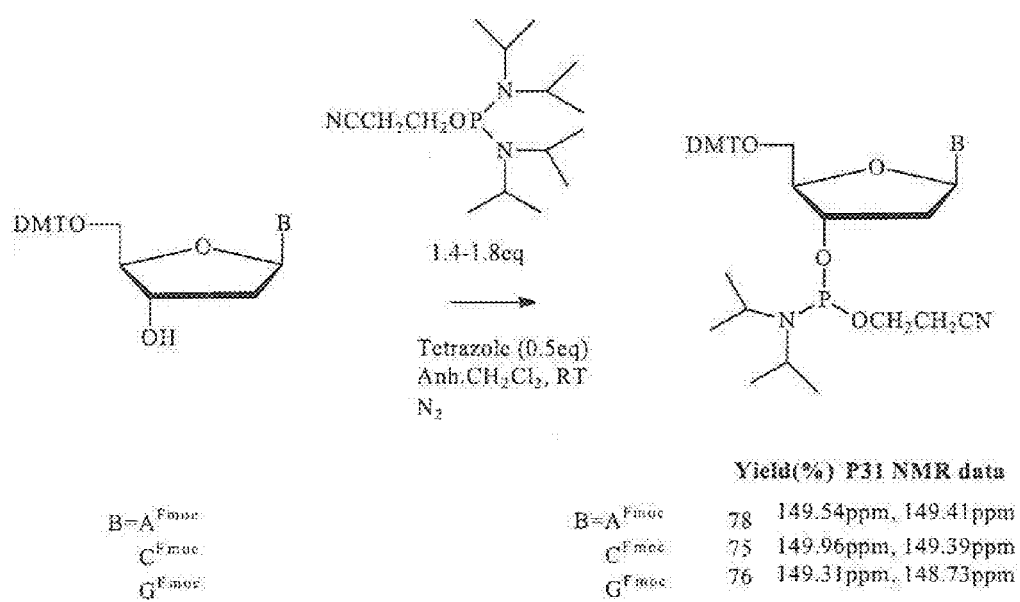
FIG. 1 schematically shows the preparation of FMOC protected deoxynucleoside phosphoramidite.

A key step in the solid support synthesis of oligonucleotides is the protection of exocyclic amino groups of 2'-deoxyadenosine, 2'-deoxycytidine and 2'-deoxyguanosine. In selected embodiments of the present invention, the labile 9-fluorenylmethoxycarbonyl group (FMOC) for the protection of the exocyclic amino functions of deoxynucleoside bases was used various protocols in the synthesis of DNA/RNA. These "FMOC based" DNA/RNA synthetic strategies may then be adapted, in selected embodiments, to a variety diagnostic and therapeutic methods. These methods include, but are not limited to, the improved synthesis of antisense compounds, high throughput DNA synthesis, the preparation of labeled nucleic acids, and the preparation and use of multifuntional columns comprising oligonucleotides bound to a solid support.

Experimental

The following protocols serve to illustrate certain preferred embodiments and aspects of the present invention and are not to be construed as limiting the scope thereof.

In the experimental disclosure which follows, the following abbreviations apply: ° C. (Centigrade); h [hour(s)]; μg (micrograms); μmole (micromoles); μl (microliters); mL or ml (milliliters); mM (milliMolar); r.t. (room temperature).

I. Use Of FMOC Derivatives in DNA/RNA Synthesis
   (Reagents and Reactions)
   A. Preparation of 5'-O-DMTR-N⁴-FMOC-2'-deoxycytidine In one embodiment, 5'-O-DMTR-N⁴-FMOC-2'-deoxycytidine was prepared according to the following protocol. 30 g (37.9 mmol) of 2'-deoxycytidine hydrochloride were sylated with trimethylchlorosilane (75 ml) in pyridine (160 ml), followed by treatment with fluorenylmethoxycarbonyl chloride (33 g, 128 mmol). After hydrolysis with $H_2O$ (300 ml) and extraction with $AcOEt/H_2O$, the $N^4$-FMOC-2'-deoxycytidine was obtained in a 97% yield (49.5 g) as a colorless powder.

For the dimethoxytritylation of the 5'-hydroxy function, 40.8 g (120 mmol) of DMTR-chloride in pyridine (100 ml) and anhydrous methylene chloride (200 ml) was used. The mixture was stirred for 30 min at room temperature to yield 74.6 g (90%) of 5'-O-DMTR-$N^4$-FMOC-2'-deoxycytidine as a white powder. Overall yield was 87% based on 2'-deoxycytidine hydrochloride. The final product, as well as all the intermediates, was fully characterized by HNMR, PNMR, MS and elemental analysis.

B. Preparation of 5'-O-(dimethoxytrityl)-$N^6$-(9-fluorenylmethoxycarbonyl)-2'-deoxyadenosine and 5'-O-dimethoxytrityl)-$N^2$-(9-fluorenylmethoxycarbonyl)-2'-deoxyguanosine In one embodiment, FMOC was used in the synthesis of 5'-O-(dimethoxytrityl)-$N^6$-(9-fluorenyl methoxy-carbonyl)-2'-deoxyadenosine and 5'-O-dimethoxytrityl)-$N^2$-(9-fluorenylmethoxycarbonyl)-2'-deoxyguanosine, and was accompanied by the formation of considerable amounts of 5'-O-DMTR-$N^6$-bis-FMOC-2'-da and 5'-ODMTR-N2-bis-FMOC-2'-dG (respectively 5-7%). All reactions were carried in one pot and gave excellent yields (e.g. greater than 75%).

C. Preparation of 3'-(2-cyanoethyl) N,N-diisopropylphosphoramidite)

For the preparation of 3'-(2-cyanoethyl) N,N-diisopropylphosphoramidite) of the protected FMOC nucleosides, diisopropylammonium tetrazolide and tetrazole were used as activating reagents during the reaction. The resulting residue was purified by flash silica gel chromatography. All resulting products were characterized by HNMR, PNMR, MS and elemental analysis.

D. FMOC Cleavage

For the cleavage of all FMOC protected 5'-O-DMTR-2'-deoxynucleoside-s, a solution of 0.05M DBU in pyridine was used. The de-protection reaction of the three mono-FMOC-protected compounds was stopped after five minutes reaction time with 0.1 M $CH_3COOH$ in pyridine and the resulting 5'-O-DMTR-2'-deoxynucleosides were isolated in 90-98% yields. The bis-FMOC-protected compounds of the 2'-deoxyguanosine and 2'-deoxyadenosine derivatives were stirred for additional five minutes with 0.05M DBU in pyridine to afford after neutralization and isolation the corresponding 5'-DMTR-deoxynucleoside in 90% yield. While it is not intended that the present invention be limited by any specific mechanism, kinetic studies shown that the fluorenylmethoxycarbonyl residue of the corresponding 5'-DMTR-2'-deoxynucleosides were substantially eliminated within two min. using a 0.05M $DBU/CH_3CN$ or Pyridine (1:1 molar ratio of 2'-deoxynucleoside/base).

E. FMOC Deprotection of 2'-dG

Figure 2:
FIG. 2 schematically shows fluorenylmethoxycarbonyl cleavage.
Figure 2:
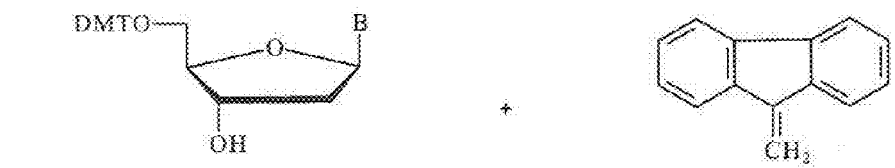

In one embodiment, the de-protection reaction of the 2'-dG compound did not take place due to the insolubility of the starting material. In this case, 0.05 M DBU/pyridine was used. All starting 2'-deoxynucleosides were dissolved within ten seconds if a higher concentration of DBU was used (e.g. 0.5 M $DBU/CH_3CN$ and a 1.20 molar ratio of deoxynucleoside to DBU). Ten seconds was sufficient to cleave of the FMOC group via elimination. On HPLC, only two peaks were detected, one for the de-blocked product and the second for the eliminated compound. In embodiments using piperidine, a slow addition of piperidine to the dibenzofulvene was observed. See FIG. 2.

II. Assembly of Oligonucleotides

The synthesis of oligonucleotides was carried out using the Ecosyn D-300 or the Ecosyn D-200 DNA/RNA synthesizers (Eppendorf Netheler Hinz GmbH, Hamburg, Germany).

A. Reagents

In some embodiments, DMTr-dA, dC, dG and T synthesis columns with a loading of 0.2 µM, DMTr-dA, dC, dG and T-β-cyanoethyl phosphoamidites, BDTD-sulfurization reagent, and all reagents for DNA synthesis and modifications on the 5'-end were purchased from Eppendorf North America (Madison, Wis., USA). dA, dC, dG and T synthesis columns containing nucleoside-derivatized synthesis support (500-1000 A pore size) and a loading of 20-30 µmole/g corresponding to 0.2 µmole nucleoside/column were purchased from Eppendorf North America (Madison, Wis., USA). β-cyanoethyl phosphoramidites (dA, dC, dG, T) were products of Eppendorf North America in prepacked bottles and anhydrous acetonitrile is added before use to yield 0.1M solutions. Before the BDTD bottle (Eppendorf North America) was attached to the port of the synthesizer, anhydrous acetonitrile is added via a dry syringe to yield a 0.1M solution. Activator solution (97% acetonitrile, 3% tetrazole), CAP A (80% tetrahydrofuran, 10% acetic anhydride and 10% pyridine) and CAP B (90% tetrahydrofuran, 10% 1-methylimidazole) solutions, 3% trichloroacetic acid in dichloromethane and oxidation reagent (80% tetrahydrofuran, 2% iodine, 5% water, 13% pyridine) were received in prepacked bottles and used as delivered from Eppendorf North America.

B. Automatic Oligodeoxynucleotide Synthesis

In some embodiments, oligonucleotides were synthesized according to the following cycle (set out in Tables 1 and 2) with repeating subroutines, whereby argon and reagent pass the column from top or bottom connection with the optosensor on or off.

TABLE 1

Column washing subroutine

| Step | Time [sec] | Source | Destination | Optosensor |
|---|---|---|---|---|
| 1 | 1 | ACN | Waste | OFF |
| 2 | 1 | GAS | Waste | OFF |
| 3 | 0 | ACN | CB | ON |
| 4 | 2 | ACN | CB | OFF |
| 5 | 4 | GAS | CB | OFF |
| 6 | 0 | ACN | CB | ON |
| 7 | 0.5 | GAS | CT | OFF |
| 8 | 0.5 | GAS | CB | OFF |
| 9 | 4 | GAS | CT | OFF |
| 10 | 0 | ACN | CB | ON |
| 11 | 3 | GAS | CB | OFF |
| 12 | 4 | GAS | CT | OFF |

CB: column bottom, CT: column top, ACN: acetonitrile

TABLE 2

Coupling subroutine

| Time | Step[sec] | Source | Destination | Mixed | Opto-sensor | Delay[sec] |
|---|---|---|---|---|---|---|
| 1 | 4 | GAS | CT | | OFF | |
| 2 | 0.2 | TET | Waste | | OFF | |
| 3 | 0 | TET | CB | NUC | ON | 10 |
| 4 | 1 | NUC | CB | TET | OFF | 10 |
| 5 | 0.1 | GAS | CB | | OFF | 10 |
| 6 | 0.1 | GAS | CB | | OFF | 10 |
| 7 | 5 | GAS | CB | | OFF | |
| 8 | 1 | GAS | Waste | | OFF | |

TET: tetrazole; NUC: phosphoramidite; CB: column bottom; CT: column top

In some embodiment, for the synthesis of thiooligos, the subroutine sequence was modified in comparison to that used for the chain elongation of unmodified oligos as follows: Deprotection, washing, coupling, sulfurization, capping.

Irrespective of the routine selected for oligonucleotide synthesis, the end procedure was as follows: (a) Cleavage of the FMOC-protection groups with 0.1 M DBU in $CH_3CN$ for 5-10 min. (b) Cleavage of the de-blocked oligonucleotide (if required) from the polymer support with concentrated $NH_3$ solution for 30 min at room temperature. The quality of the synthesized oligonucleotides was evaluated by PAGE, HPLC, CE and the biological activity may be proven by the synthesis a gene (or portion thereof).

It should also be noted that the polymer supports are important in the methods, described by the present invention, for the direct immobilization of oligonucleotides. Moreover, the present invention incorporates an improved process for the derivatization of different types of silica gel and controlled pore glass. Specifically, this improved process both keeps the silica particles intact and also reduces the consumption of reagents.

III. Functionalization of Polymer Supports on Gas Phase: Silica Gels and Controlled Pore Glasses

A. Surface Activation 3 grams of silica gel, controlled pore glass (native), or polystyrene based supports were suspended in concentrated hydrochloric acid solution (30 ml. 25.degree. C., 30 min). The activated material was recovered by filtration and washed with distilled water (200 ml), methanol (40 ml) and dried in vacuo.

B. Gas-Phase Aminopropylsilylation

Activated silica gel or controlled pore glass (2 g) was placed in a 20.times.150 mm pyrex tube containing 3-aminopropyl triethoxysilane (3 ml). A hose was fitted onto the end of the tube and the vessel and contents were sealed under vacuum using a flame. The tube was incubated behind a safety shield (140.degree. C., 12 h) and the reaction was terminated by returning to ambient temperature. Silica or controlled pore glass was recovered by cautiously cracking open the vessel. Each derivative was washed with distilled water (200 ml), ethanol (40 ml) and ether (20 ml) and dried in vacuo.

C. Gas-Phase Succinylation

Aminopropylsilylated silica gel or controlled pore glass (2 g) was sealed in vacuo in a pyrex tube containing succinic anhydride (200 mg). A hose was fitted onto the end of the tube and the vessel and contents were sealed under vacuum using a flame. The reaction was incubated overnight (140.degree. C., 16 h) and terminated by returning to ambient temperature and cracking open the vessel. The material was washed and dried as described above.

D. Conventional Aminopropylsilylation and Succinilation

Figure 5:
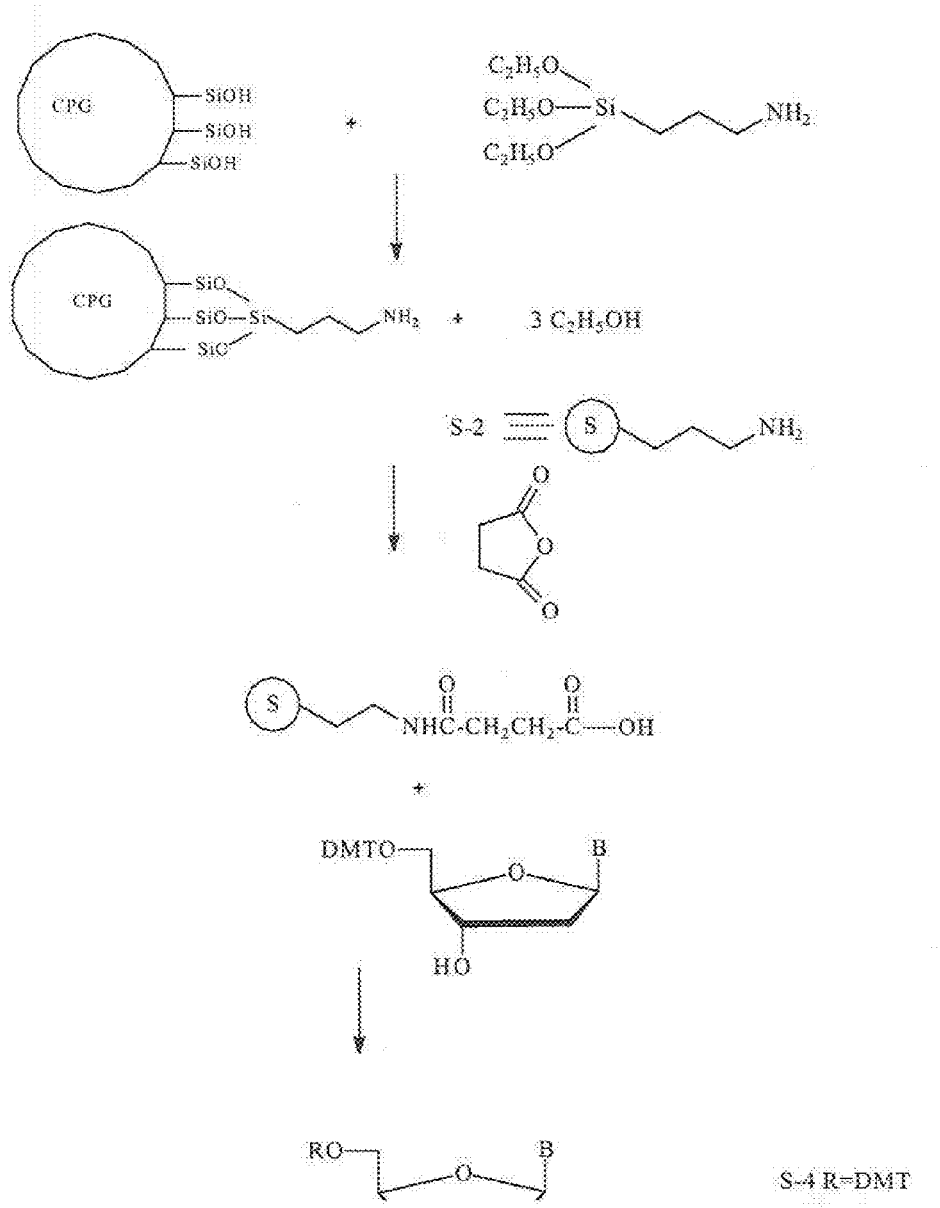
FIG. 5 is a schematic overview of the protocol for the aminopropylsilylation of silica gel (or controlled pore glass).

Silica gel or controlled pore glass starting material was aminopropylsilylated, in refluxing toluene and succinilated in water, according to the following protocol (as set out in the schematic overview projected in FIG. 5).

Figure 4:
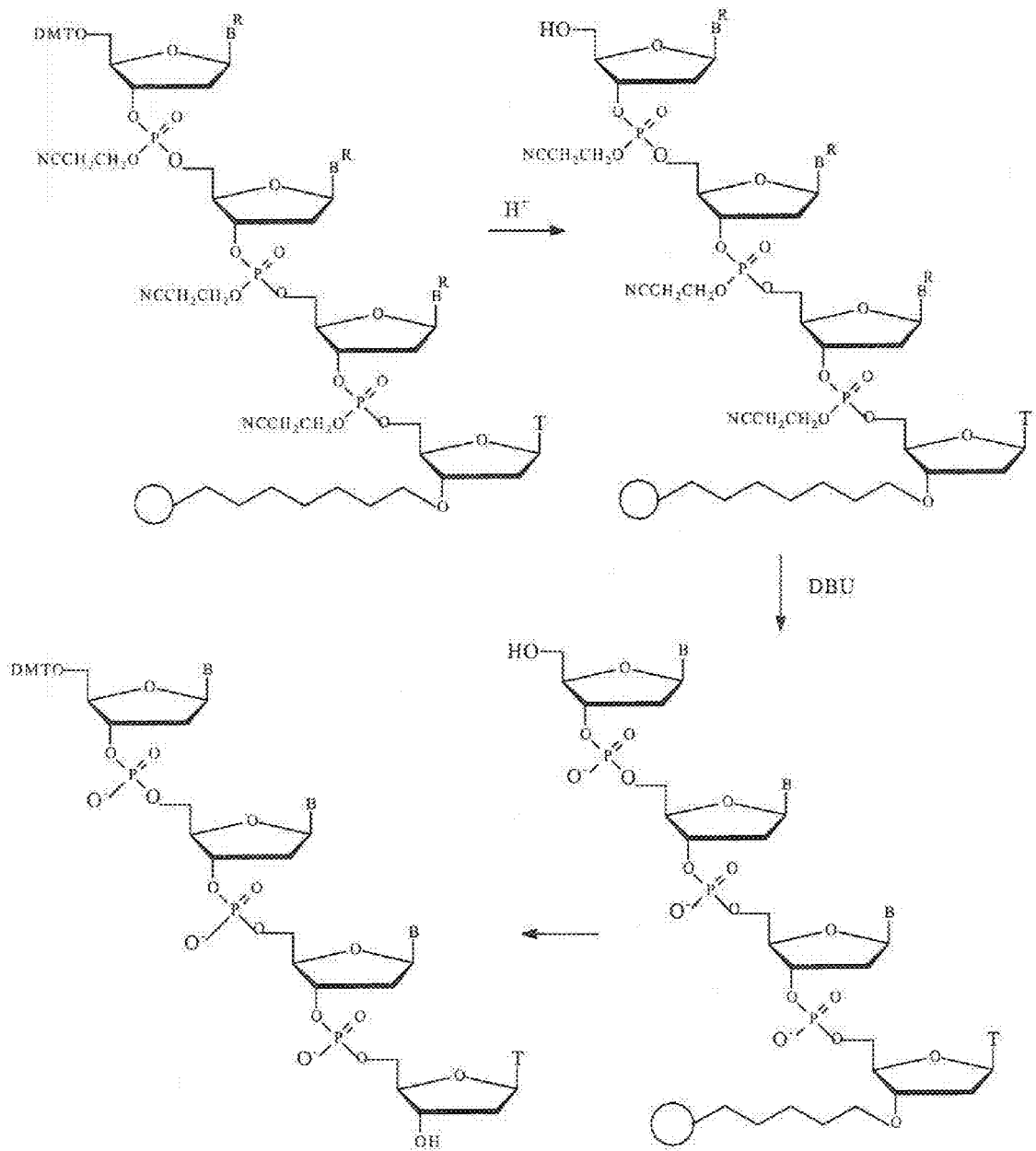
FIG. 4 is a schematic of the full deprotection "FMOC Strategy" used in the synthesis of oligonucleotides with the option, if desired, of cleavage.

Silica gel was surface activated by refluxing with HCl, thereby providing the active SiOH groups on the surface of the silica gel. This activated gel (see, S-1 in FIG. 4) is derivatized by refluxing with .gamma.-aminopropyltriethoxysilane in toluene to provide the functionalized resin (see, S-2 in FIG. 4). The amino group may be derivatized in a number of ways, including a standard procedure with succinic anhydride to give the activated resin (see, S-3 in FIG. 4). The final step in preparing the resin for use in the automated procedure requires condensing a protected nucleoside to S-3, with dicyclohexylcarbodiimide (DCC) used as the condensing agent in pyridine. When diethylaminopyridine is used as catalyst, the resulting resin (see, S-4 in FIG. 4) contains approximately 0.1 millimole of nucleoside per gram of resin. On removal of the dimethoxytrityl group (DMT) from the nucleoside with mild acid, the resin S-5 that is obtained is ready for chain extension. 10 milligrams of the resin (see, S-5 in FIG. 4) was packed into a synthesis column which snaps into the synthesizer.

Once the resin (see, S-5 in FIG. 4) has been attached to the instrument, the chain may be synthesized.

IV. Methods Designed to Capture Nucleic Acid Sequences

In selected embodiments, the present invention contemplates a single stranded oligonucleotide bound to a polymer support. Such oligonucleotide is complementary to a specific sequence on a target nucleic acid that (in a preferred embodiment) is longer than the oligonucleotide immobilized on the solid support. This design allows for the selective hybridization of the target nucleic acid to the oligonucleotide on the support.

The present methods of directly immobilizing oligonucleotides, of a specific sequence, are particularly useful for the isolation of a single stranded nucleic acid sequence or to detect the presence of a particular nucleic acid present in a relatively low concentration. The use of the FMOC-protected phosphoramidites allows the direct synthesis of any oligonucleotide and, after de-protection under organic conditions, to keep the oligonucleotide attached to the polymer support (controlled pore glass [CPG], polystyrene, tentagel, silica gel, membranes, etc.)

Given the highly labile character of FMOC, the final de-protection may be carried out under organic conditions (e.g. 10% piperidine in dichloromethane or dimethyl formamide or 1.0 M DBU in acetonitrile). The derivatization of the polymer support for the direct immobilization of oligonucleotides was completed via LCMA according to the following protocol.

A. Derivatives of LCAMA-CPG and of 5'-O-(2-Dansylethoxycarbonyl)-2'-deoxy-3' O-succinyinucleosides To a mixture of 200 mg of LCAMA-CPG [e.g. (long-chain-alkyl)methylamine controlled-pore glass)], 45 µmol of Thy (29 mg), $Cyt^{npeoc}$ (37 mg), $Ade^{npeoc}$ (38 mg), or $Gua^{nPe}/_{npeoc}$ (46 mg), and 30 mg (91.4 µmol) of TOTU, 3 ml of abd. MeCN and 19 µl (180 µmol) of N-methylmorpholine were added. After a short ultrasonic treatment (30 s) and 2 h standing in the dark at r.t., the CPG material was collected in a glass suction filter and washed with MeOH, DMF, MeOH, and $Et_2O$.

V. Preparation of Immobilized Oligonucleotides to Capture RNA

The m-RNA of higher cells is usually polyadenylated to a various degree at its 3' end (known as the Poly A-tail or track). The present invention contemplates isolating m-RNA by hybridization (binding/basepairing) to the immobilized oligonucleotides synthesized as described above. In this manner, m-RNA (PolyA+RNA) hybridizes with its complementary sequence or with any specific sequence linked to a solid support (such as silica gel). When using an oligonucleotide attached to a polymer support, the target m-RNA becomes immobilized to the support and can then be separated by removing the liquid phase containing all the non bound nucleic acids from the hybridization mixture. After all of the remaining liquid has been removed, the polyA+RNA or any specific RNA can be eluted from the oligo-dT20/30 or specific m-RNA probe support. This allows the physical separation of polyA+RNa from non-polyadelynated, non-binding RNA.

VI. Oligonucleotide Synthesis, Purification and Phosphorylation

Oligonucleotides were synthesized using the FMOC derivative cyanoethyl phosphoramidites as described above. For all the oligonucleotides the average stepwise yield based on tritanol release was higher than 99.4%. The de-protection was performed with a solution of 0.1 M DBU in acetonitrile. Cleavage of the oligonucleotide was performed in the presence of ammonium hydroxide for 30 min. at room temperature. Synthesis was performed in a 150 nmol scale on CPG-1000.

The crude oligonucleotides were purified by polyacrylamide gel electrophoresis. The oligonucleotides, ranging in length from 9 to 84 nt and sharing 9 to 15 complementary overlapping bases, contained several repeat sequences such as CGGC (6 times), GCGGC (3 times), TCTGCGGCG (2 times) and GCGCCCGC (2 times). Oligonucleotides phosphorylation was effected using bacteriophage T4 polynucleotide kinase (Gibco, Gaithersburg, Md., USA). Annealing and ligation was carried out with Ampligase TM DNA ligase (Epicentre Technologies, Inc. Madison, Wis., USA).

Cloning of the ligated sequences: For direct cloning, the assembled blocks from the previous reaction were ligated to SmaI and SstI digested vector pGEM4Z using T4 DNA ligase at 16° C. overnight.

VII. Antisense Applications

In some embodiments, the present invention contemplates the targeting of therapeutic gene products [including, but not limited to, Human Insulin-like Growth Factor I (IGF-I)]. For example, in some embodiments, the present invention contemplates compositions comprising oligomeric antisense compounds, particularly oligonucleotides (for example, those identified in the drug screens), for use in modulating the function of nucleic acid molecules encoding IGF-I, ultimately modulating the amount of IGF-I expressed. This is accomplished by providing antisense compounds that specifically hybridize with one or more nucleic acids encoding IGF-I.

The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more MRNA species, and catalytic activity that may be engaged in or facilitated by the RNA. The overall effect of such interference with target nucleic acid function is modulation of the expression of IGF-1.

In the context of the present invention, "modulation" means either an increase (stimulation) or a decrease (inhibition) in the expression of a gene. It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or MRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., detection or modulation of expression of the protein, will result.

Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an MRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an MRNA in the 5' direction from the translation initiation codon, and thus including nucleotides between the 5' cap site and the translation initiation codon of an MRNA or corresponding nucleotides on the gene, and the 3' untranslated region (3' UTR), referring to the portion of an mRNA in the 3' direction from the translation termination codon, and thus including nucleotides between the translation termination codon and 3' end of an MRNA or corresponding nucleotides on the gene. The 5' cap of an mRNA comprises an N7-methylated guanosine residue joined to the 5'-most residue of the mRNA via a 5'-5' triphosphate linkage. The 5' cap region of an MRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous MRNA sequence. MRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

The present invention contemplates that modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts and free acid forms are also included.

It is also contemplated that modified oligonucleotide backbones (that do not include a phosphorus atom therein have backbones that are formed by short chain alkyl or cycloalkyl internucleoside linkages) mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Specifically, the present invention contemplates the use of FMOC-protected phosphoramidites for the synthesis of antisense compounds corresponding to the "RO-P-O" backbone of DNA wherein (in preferred embodiments R is selected from the group consisting of methyl, ethyl, akly, and aryl group. While it is not intended the present invention be limited by any specific mechanism, the FMOC derivatives described in the present invention facilitate deprotection under organic conditions.

Figure 3:
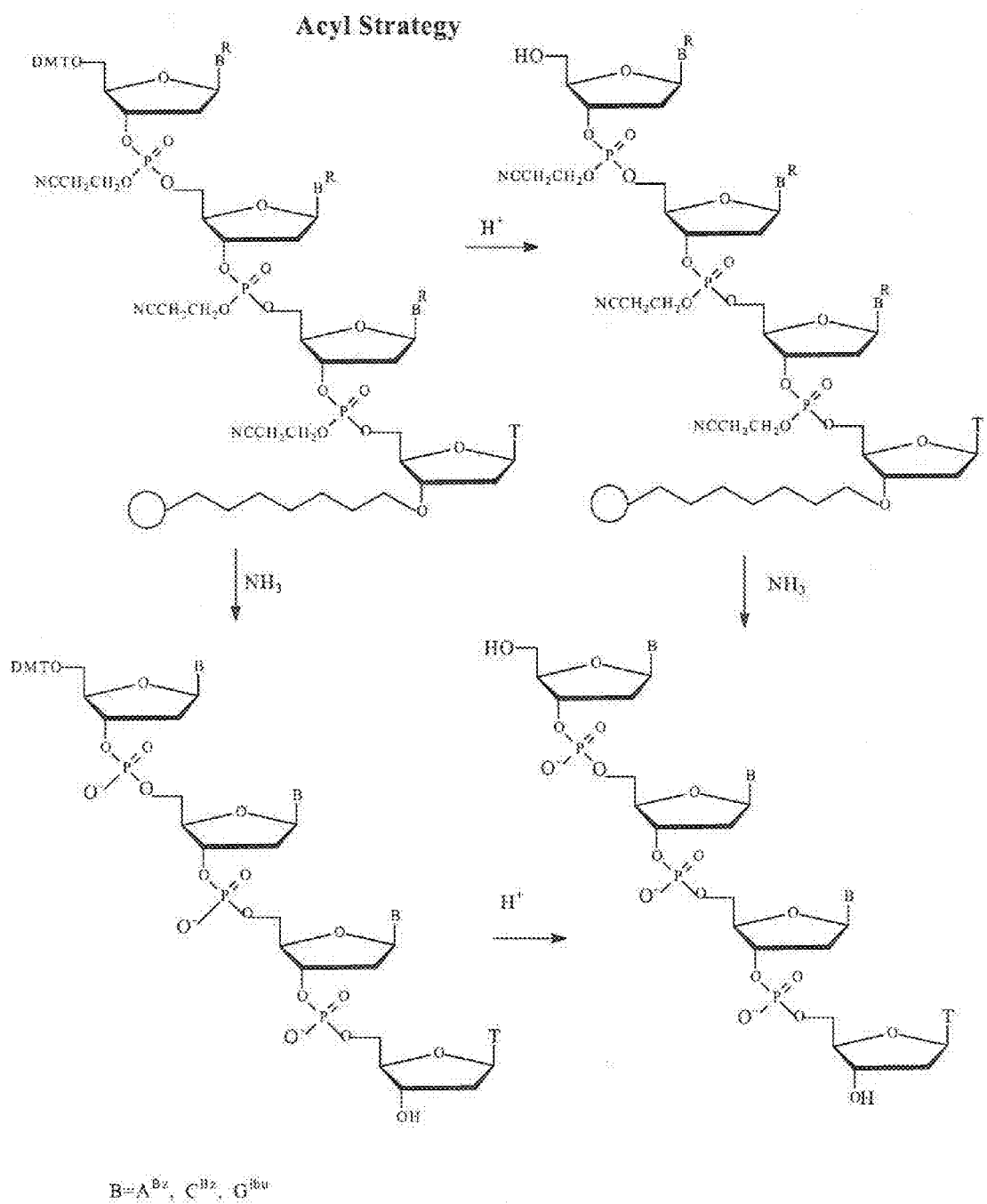
FIG. 3 is a schematic of the traditional cleavage and deprotection "Acyl Strategy" used in the synthesis of oligonucleotides.

That is to say, standard protocols for deprotection, i.e. using ammonium hydroxide, are characterized by cleavage followed by deprotection. Specifically, the deprotection of the protecting groups on the phosphorous and the exocyclic amine (using these standard protocols) occur at the same time. That is to say, using the traditional "Acyl Strategy" there is no deprotection without cleavage. See, for example, the "Acyl Strategy" schematic presented in FIG. 3. In contrast, using the FMOC protected phosphoramidites described in the present invention, the deprotection selectively occurs first on the exocyclic amino groups; leaving intact the protection on the phosphorous. It should be noted, however, the use of DBU in $CH_3CN$ cleaves both FMOC and the cyanoethyl group from the phosphate (of the phosphoramidite). That is to say, in embodiments using DBU, an active oligonucleotide is produced when the FMOC and the cyanoethyl group are cleaved, by DBU, from the phosphate of the phosphoramidite. See, for example, the "FMOC Strategy" presented in FIG. 4.

In some embodiments it may be desirable to remove (using piperidine instead of DBU) only the FMOC group from the exocylic amine of the phosphoramidite, thereby, leaving the alkyl residue on the phosphate of the phosphoramidite such that the phosphate is protected by the cyanoethyl group in this particular embodiment. These embodiments are especially suited to evaluating the antisense properties of a given oligonucleotide such that the phosphate groups of said oligonuleotide are protected, only, with said cyanoethyl group or any other alkyl residue.

One skilled in the relevant art knows well how to generate oligonucleotides containing the above-described modifications. The present invention is not limited to the antisense oligonucleotides described above. Any suitable modification or substitution may be utilized.

Furthermore, it is not necessary for all positions in a given compound to be uniformly modified, and in fact more than one of the aforementioned modifications may be incorporated in a single compound or even at a single nucleoside within an oligonucleotide. The present invention also contemplates antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results could be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The chimeric antisense compounds contemplated by the present invention may be formed as composite structures of two or more oligonucleotides, modified oligonucleotides, oligonucleosides and/or oligonucleotide mimetics. The present invention also contemplates pharmaceutical compositions and formulations comprising the antisense compounds of the present invention.

VII. High Throughput DNA Synthesis

The present invention contemplates the use of FMOC derivatives in the high throughput synthesis of DNA. It is not intended that the present invention be limited to any specific format for high throughput synthesis. In one embodiment, a standard 96-well plate is contemplated as the solid support to which oligonucleotides are synthesized using the FMOC protocols elaborated above. The adaptation of these FMOC protocols to oligonucleotide synthesis in a 96 well plate offers advantages over standard conditions which rely on the use of ammonium hydroxide concentrated at 55° C. for 16 h and the use of methyl amine:ammonium hydroxide (9:1 v/v) at 95° C. for one hour.

The use, in these standard methods, of ammonium hydroxide and a mixture of methyl amine and ammonium hydroxide (both highly volatile reagents) promotes leakage between reaction well and is therefore problematic (especially in 96-well format). Specifically, this leakage problem can cause the incomplete deprotected of oligonucleotides. The FMOC chemistry described in the instant application, in contrast, facilitates the complete deprotection of oligonucleotides at room temperature (with an organic reagent: 0.1 M DBU/Acetonitrile) substantially without leakage.

Moreover, this FMOC synthetic motif allows for the production of multifuntional columns. That is to say, if oligonucleotides are immobilized on polymer resins suitable for incorporation into flow through columns these immobilized oligonucleotides (synthesized using the FMOC chemistries described in the instant application) may be washed, and thereby purified, while still attached to the resins comprising the column. In this way a multifuctional column is created such that the same column may be used for the synthesis and purification of a given oligonucleotide. In one embodiment of the present invention these substantially purified, but immobilized, oligonucleotides are cleaved from their solid support by eluting the column with ammonium hydroxide.

In other embodiments, FMOC protected phosphoramidites eliminate the erosion, once again caused by the use of ammonium hydroxide in the final deprotection, observed in traditional microbiochip manufacturing wherein oligonucleotides are immobilized on a silicon "chip".

IX. Preparation of Labeled Nucleic Acids

FMOC phosphoramidites may be incorporated with various labels, thereby, creating a "reporter molecule". These labels include, but are not limited to: $^{32}P$, $^{33}P$, $^{35}S$, enzymes, or fluorescent molecules (e.g., fluorescent dyes). Once again, the incorporation of detectable labels with FMOC phosphoramidites (described in the instant application) confers decided advantages over traditional labeling techniques. Specifically, theses traditional labeling techniques use sodium hydroxide as a methanolic solution for deprotection in a reaction that occurs at room temperature for 18 h. Under these relatively "harsh" conditions, the cleavage of the label, from the oligonucleotide, is impossible to avoid. These traditional labeling techniques typically provide recovery of labeled product in the range of 20-30%. Using the relatively "milder" conditions characterized by the chemistries of the present invention, almost 100% of the synthesized labeled oligonucleotide may be recovered.

In other embodiments, it is contemplated that FMOC phosphoramidites may be incorporated into fluorescence in situ hybridization (e.g. "FISH"), a technique in which detectably labeled DNA probes (which can be prepared, for example, from cDNA sequences or genomic sequences contained in cosmids or bacterial artificial chromosomes (BACs)) are hybridized to cytogenetic or histological specimens. Such specimens include, but are not limited to, metaphase chromosome spreads and interphase nuclei prepared from tissue or blood specimens, and formaldehyde-fixed, paraffin-embedded tissue sections. Fluorescent labels can be directly incorporated into the probe, or can be applied as antibody-label conjugates which bind to affinity labels (for example, biotin or digoxigenin) incorporated into the probe, either directly, or as an antibody "sandwich" (i.e. a primary and a secondary antibody). The fluorescent dyes include, but are not limited to rhodamine, texas red, FITC (fluorescein isothiocyanate) and TRITC (tetramethyl rhodamine isothiocyanate). The fluorescent labels are detected using a fluorescence microscope equipped with a mercury or xenon lamp (as an illumination source) and appropriate filters for excitation and emission. The pattern of fluorescence can be used to assess copy number of the locus recognized by the probe, or, in cases where two or more (differentially) labeled probes are used, to assess the relative positions of the probes (for example to detect chromosomal rearrangements, such as translocations and inversions).

From the above, it should be evident that the present invention provides compositions and methods that allow for efficient (i.e., high yield) synthesis of DNA/RNA using FMOC derivatives. The present invention provides compositions and methods which provide high quality, high volume preparations of DNA/RNA. This recovered DNA/RNA, in turn, can be used in a variety of diagnostic and therapeutic methods.

The invention claimed is:

1. A method for synthesizing and purifying a phosphotriester oligonucleotide immobilized on a solid support complex, comprising:
   a) providing i) a polymer support, and ii) four pools of nucleoside 3'-monomers in solution, said monomers having a nucleoside base and a phosphoramidate group, wherein at least one of said monomers contains 9-fluorenylmethoxycarbonyl as an amino protecting group on the monomer base, and said monomers have an alkyl residue on the phosphate of the phosphoramidite group;
   b) sequentially contacting said polymer support with a solution of monomers from one or more of said four pools under conditions such that a sequence of monomers is immobilized on said polymer support to generate an oligonucleotide/polymer support complex, wherein said complex comprises at least one monomer containing 9-fluorenylmethoxycarbonyl base protecting group and wherein said solution, after said contacting, comprises unreacted material;
   c) treating said complex under conditions such that said unreacted material is substantially removed, thereby creating a purified oligonucleotide/polymer support complex, and
   d) treating said purified oligonucleotide/polymer support complex under conditions whereby said 9-fluorenylmethoxycarbonyl, but not the phosphoramidate alkyl residue, is released.

2. The method of claim 1, wherein said nucleoside 3'-phosphoramidite monomer containing 9-fluorenylmethoxycarbonyl as an amino protecting group is a 9-fluorenylmethoxycarbonyl-2'-cytidine 3'-phosphoramidite.

3. The method of claim 1, wherein said nucleoside 3'-phosphoramidite monomer containing 9-fluorenylmethoxycarbonyl as an amino protecting group is a 9-fluorenylmethoxycarbonyl-2'-adenosine 3'-phosphoramidite.

4. The method of claim 1, wherein said deoxyribonucleoside 3'-phosphoramidite monomer containing 9-fluorenylmethoxycarbonyl as an amino protecting group is a 9-fluorenylmethoxycarbonyl-2'-guanosine 3'-phosphoramidite.

\* \* \* \* \*